United States Patent [19]
Welker

[11] Patent Number: 5,945,611
[45] Date of Patent: Aug. 31, 1999

[54] DUAL PISTON FLOW-THROUGH SAMPLER

[75] Inventor: Brian H. Welker, Sugar Land, Tex.

[73] Assignee: Welker Engineering Company, Sugar Land, Tex.

[21] Appl. No.: 09/115,818

[22] Filed: Jul. 15, 1998

[51] Int. Cl.[6] .................... G01N 1/20; G01N 1/14
[52] U.S. Cl. .................... 73/864.33; 73/863.71; 73/863.84; 73/864.35
[58] Field of Search .................... 73/863.71, 863.84, 73/864.33, 864.34, 864.35

[56] References Cited

U.S. PATENT DOCUMENTS

| | | | |
|---|---|---|---|
| 2,986,940 | 6/1961 | Russell | 73/422 |
| 3,218,868 | 11/1965 | Gill | 73/422 |
| 3,429,186 | 2/1969 | Price et al. | 73/421.5 |
| 3,638,498 | 2/1972 | Nelms | 73/422 |
| 4,244,224 | 1/1981 | Conn | 73/422 |
| 4,269,064 | 5/1981 | Johnson et al. | 73/422 |
| 4,531,895 | 7/1985 | Zeck | 417/401 |
| 4,628,750 | 12/1986 | Welker | 73/863.71 |
| 4,744,255 | 5/1988 | Jaeger | 73/863.84 |
| 5,191,801 | 3/1993 | Allen et al. | 73/864.35 |
| 5,366,904 | 11/1994 | Qureshi et al. | 73/864.35 |
| 5,460,054 | 10/1995 | Tran | 73/863.33 |
| 5,641,894 | 6/1997 | Hosokawa | 73/863.84 |
| 5,792,942 | 11/1998 | Hosokawa | 73/863.84 |

*Primary Examiner*—Hezron Williams
*Assistant Examiner*—Chad Soliz
*Attorney, Agent, or Firm*—Herzog, Crebs & McGhee, LLP; Bruce E. Burdick; Matthew A. Rosenberg

[57] ABSTRACT

A device for introducing a sample into or removing a sample from a pipeline, tube, or the like, and more particularly to a device for sampling fluids under pressure in a pipeline, tube, duct, conduit, or the like.

31 Claims, 2 Drawing Sheets

DUAL PISTON FLOW-THROUGH SAMPLER

BACKGROUND OF THE INVENTION

1. Field of the Invention

The present invention relates to fluid sampling devices, and more particularly to a device for sampling fluids under pressure in a pipeline, tube, duct, conduit, or the like.

2. Description of the Related Art

Fluids flowing through pipelines or tubes often need to be sampled to determine the composition of the fluid being transported. For example, payments for gas delivered from a gas pipeline may depend on the BTU energy level of the gas transported through the line. It is desirable to be able to sample the fluid in the pipeline easily and repeatedly without opening the pipeline, which is often under pressure. Because the composition of the transported fluid often varies with time, it is particularly important that the sample be representative of the fluid in the pipeline, and thus that the sampling method minimize dead volume in the sampler. Likewise, it is desirable that the flow paths be relatively straight and unobstructed to minimize the effect of any debris present in the pipeline and to facilitate cleaning of the pipeline. It is also desirable that the sample be of a predetermined size and be periodically taken on a timed basis. How to accommodate all of these competing interests in a pipeline fluid sampler is not currently known and not currently obvious to pipeline accessory engineers.

Thus there is a need for a device that permits removal of samples from pipelines, tubes, and the like without opening them and minimizing dead volume to prevent cross contamination of samples.

Some conventional sampling systems have two pistons in a common passageway, with one having a tubular shaft mounted coaxially on the solid shaft of the other. This passageway is a side passageway through which fluid is only intended to flow during sampling. This side passageway intersects a main flow passageway, which is being sampled. The piston closest to the main passageway moves out of the side passageway and into the main passageway to expose the space in the side passageway between the pistons to the fluid sample. The piston furthest from the main passageway allows flow into, but blocks flow through, the side passageway. Then both pistons are simultaneously drawn into the side passageway in a spaced relationship to capture a sample in the annular space in the side passageway between the pistons. The pistons are aligned with a lateral port in the side passageway and moved toward each other to force a sample of fluid out through the port. There is no continuous fluid flow through the side passageway, as the side passageway is either open only to the main passageway, open only to the outlet port, or open to neither outlet port nor main passageway.

Another prior sampling system has lateral inlets and outlets to a sampling passageway between the inlets and outlets. This has no pistons, the sampling being done by pressure responsive valve timers. This method results in a variable quantity of sample depending on pressure in the line being sampled, and depends on the pressure in the sample container being lower than that in the line being sampled. At least three separate pressure responsive valves and a lengthy sample line are required.

It is thus seen that no solution to the lack of a sample having a continuous through flow with no obstructions and intermittent set volume sampling with negligible sample cross contamination.

SUMMARY OF THE INVENTION

The present invention addresses these needs through having a chamber with an inlet port, an outlet port, a sample port between the inlet outlet ports, and two opposed pistons, the pistons simultaneously operative to close off the inlet and outlet ports and to force a given sample volume through the outlet port.

It is thus an object of the present invention to provide a sampler that can be used in a pipeline without opening the pipeline.

It is another object of the present invention to provide a sampler that minimizes dead volume to reduce cross-contamination of later samples by earlier ones.

It is further an object of the invention to provide a means of introducing a sample into a pipeline without allowing inadvertent admission of air.

It is yet another object of the invention to provide a means of introducing a sample into a pipeline with minimal turbulence.

The present invention meets the above objects by providing a way to remove fluid from a pipeline through a sample port that communicates with a region outside of the pipeline and also with a common passageway in which opposed pistons move without opening the pipeline to the region.

The present invention further meets the above objects by providing a common passageway through which the fluid to be sampled can flow and rejoin the main stream. This helps flush the passageway of any residuum from an earlier sample and provides a purer and fresher sample more representative of current condition in the pipeline at the time of sampling.

It further meets the above objects by allowing introduction of a sample through the sample port from the common passageway while that passageway is temporarily sealed from the main flow of the pipeline. Re-establishment of communication between the common passageway and the interior of the pipeline introduces new fluid into the common passageway and flushes any remaining sample from the common passageway into the main flow within the pipeline. The flow path through the common passageway is direct enough to avoid much residue collection and to minimize turbulence.

BRIEF DESCRIPTION OF THE DRAWINGS

So that the manner in which the above recited features, advantages and objects of the present invention are attained and can be understood in detail, a more particular description of the invention briefly summarized above, may be had by reference to the embodiment thereof that is illustrated in the appended drawings, wherein.

It is to be noted, however, that the appended drawings illustrate only a typical embodiment of the invention and that they are therefore not to be considered limiting of its scope, for the invention may admit to other equally effective embodiments.

DETAILED DESCRIPTION OF THE INVENTION

Figure 1:
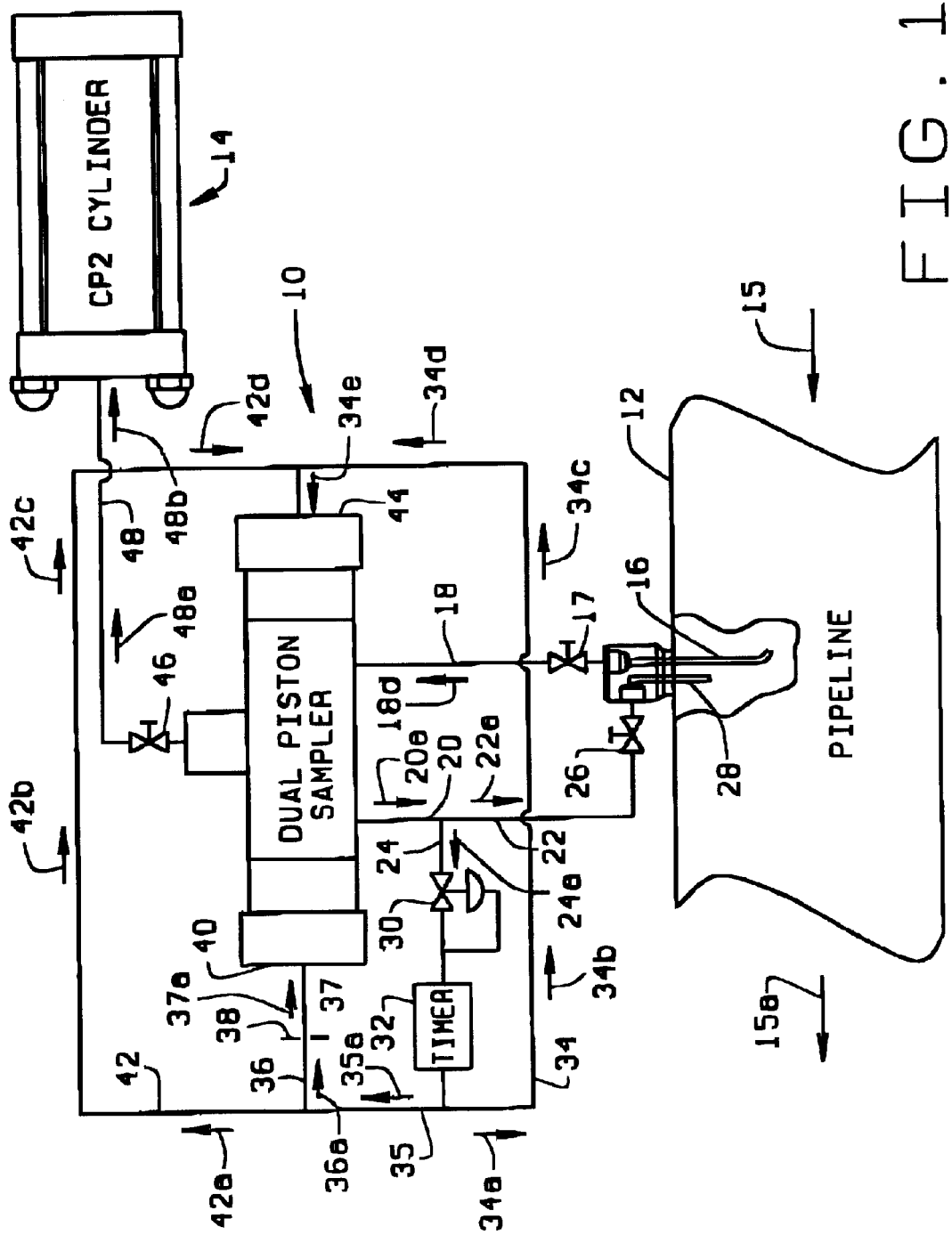
FIG. 1 is a schematic flow diagram showing the relationship of the dual piston sampler of a preferred embodiment of the invention to a pipeline.

Referring to FIG. 1, fluid flowing in pipeline 12 in direction 15 flows through pitot tube 16 and control valve 17 into inlet line 18 in direction 18d to enter sampling system 10. Fluid returns from sampling system 10 through outlet line 22 in direction 22a through outlet control valve 26 through outlet tube 28 to rejoin the main stream in pipeline 12 flowing in direction 15a.

When a sample is desired, sampling rate timer 32 opens fluid communication in line 24 to allow fluid from outlet line 20 to flow in direction 20a through power supply line 24 and pressure regulator valve 30 in direction 24a and into primary first piston power supply line 34 and primary second piston power supply line 35. Fluid flowing in primary first piston power supply line 34 in directions 34a–e enters first end cap 44, along with fluid flowing in primary second piston power supply line 35 in directions 35a and fluid flowing in secondary first piston power supply line 42 in directions 42a–d. Fluid flowing in primary second piston power supply line 35 in direction 35a also enters primary second piston power supply line 36 in direction 36a, passes through orifice 38, and travels through reduced flow primary second piston power supply line 37 in direction 37a before entering second end cap 40. Fluid flowing through second piston power supply line 37 and primary first piston power supply line 34 forces, in a manner described below, a sample through sampler shutoff valve 46 into sample flow line 48 in direction 48a–b and then into sample cylinder 14. After the sample is taken or after sample cylinder 14 becomes full, sampler shutoff valve 46 can be closed to allow the sample container to be removed and, if desired, replaced.

Figure 2:
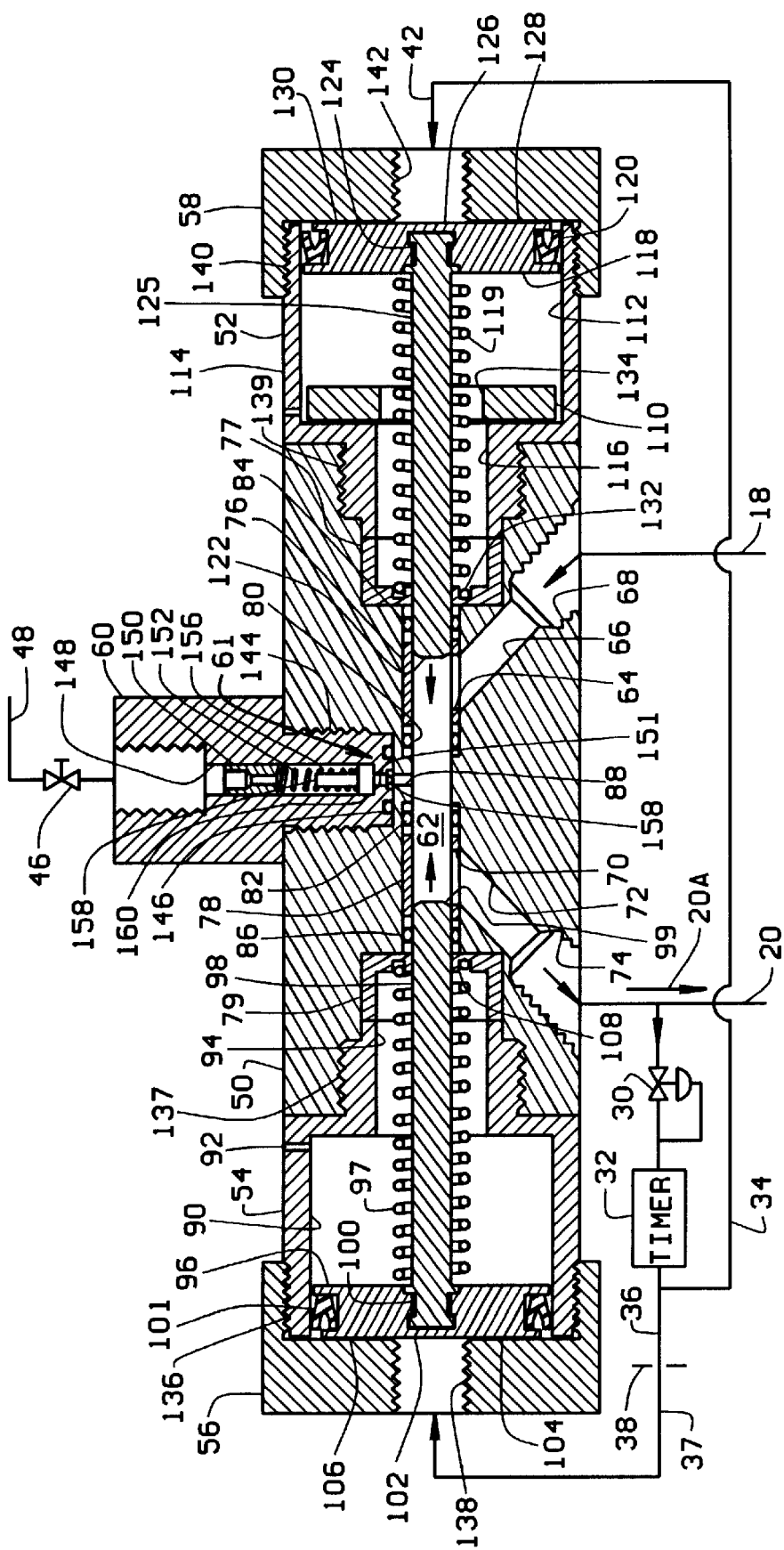
FIG. 2 is a front longitudinal diametric cross-sectional view of the dual piston sampler of FIG. 1.

Referring to FIG. 2, a more detailed view of the sampler 10 is shown, excluding the second supply line 42, which is merely indicated on the right side of the drawing. Inlet line 18 engages inlet passageway 66 of sampler body 50 with threads 68. Similarly, outlet line 20 engages outlet passageway 72 with threads 74. In normal operation prior to sampling, first piston 118 and second piston 96 are retracted to expose inlet opening 64 and outlet opening 70. Fluid from inlet line 18 passes through inlet passageway 66 and inlet opening 64 to enter sample chamber 62, and continues through outlet opening 70 into outlet passageway 72 and thence to outlet line 20 in direction 20a. This provides a continuous flushing action to clean the sample chamber 62 between samples and to continually provide a fresh current sample to sample chamber 62.

When a sample is desired, sampling rate timer 32 opens to permit fluid from pressure regulator valve 30 to enter primary first piston power supply line 34 in direction 34a–e and primary second piston power supply line 35 in direction 35a. Valve 30 serves to prevent overpressurization of the power supply lines and pistons. Referring again to FIG. 1, fluid from primary second piston power supply line 35 enters primary second piston power supply 36 in direction 36a, proceeds through orifice 38, and enters second piston power supply line 37 in direction 37a. As seen in FIG. 2, second piston power supply line 37 engages second end cap 56 at threaded center opening 138, whereby fluid from second piston power supply line 37 impinges on outer face 102 of second piston 96. Relief grooves 104, 106 allow this pressure to contact the entire outer face 102 of piston 96. Similarly, primary first piston power supply line 34 engages first end cap 58 through threaded center opening 142, whereby fluid from primary first piston power supply line 34 is made to impinge on outer face 126. Relief grooves 128 and 130 allow this pressure to act upon the entire outer face 126 of piston 118.

Threaded connections 139,137 connect first cylinder 52 and second cylinder 54 to sampler body 50. First end cap 58 and second end cap 56 engage first cylinder 52 and second cylinder 54 through threaded connections 140 and 136, respectively. Connections 124,100 connect first piston 118 and second piston 96 to first piston rod 125 and second piston rod 98, respectively. Piston rods 125, 98 move within inner portion 80 of first sleeve 76 and inner portion 82 of second sleeve 78 of common passageway 62. First piston rod O-ring seal 84 and second piston rod O-ring seal 86 seal their respective piston rods within sampler body 50. Fluid pressure applied to outer faces 102,126 of pistons 96,118 moves pistons 96,118 toward each other against biasing force exerted by first spring 119 and second spring 97, which are held within first spring retainer cup 77 by groove 132 and within second spring retainer cup 79 by groove 108, respectively. In so doing, first piston 118 necessarily moves quicker than second piston 118 due to the pressure reduction caused by orifice 38 in line 37 to second piston 96 reducing the volume of first low pressure chamber 112 and second low pressure chamber 90, respectively. Elastomeric chevron piston sealing rings 101,120 make gas-tight seals to pistons 118, 96. Fluid pressure forces first piston 118 to move through center opening 134 of spacer 110, which stops first piston 118 at the point where first inner piston face 122 just occludes inlet opening 64, thereby sealing off the inlet side of central passageway 62 from inlet line 18. Fluid pressure on second piston 96, being reduced by orifice 38, moves second piston 96 into central passageway 62 more slowly than first piston 118 until second inner piston face 99 moves completely against the face 122 of the right piston to seal off line 20 and push the sample out through sampling side port 88 and sampler valve body 61. Thus orifice 38 acts as a delay means to retard the motion of second piston 96 relative to first piston 118. This could also be accomplished by having a stiffer spring 97 than spring 119 so that the difference in spring constants served as the delay means. Other suitable delay means could also be used, such as an additional spring on piston 96 or an additional supply line 42 as in FIG. 1 to the first piston.

Motion of first piston 118 to the left, or inward, compresses first spring 119 into reduced diameter portion 116 of first low pressure chamber 112, while vent 114 allows gas to escape.

Similarly, motion of second piston 96 to the right, or inward, compresses second spring 97 into reduced diameter portion 94 of low-pressure chamber 90, with vent 92 permitting gas to escape.

Sampler port body 60 engages sampler body 50 through threaded connection 144, while inner end 151 of sampler port body 60 allows communication of sampler port body 60 with common passageway 62. Seal 146 prevents leakage between sampler port body 60 and sampler body 50. Fluid forced by pistons 118, 96 through sampling side port 88 pushes valve body 156 away from flange 160 on valve seat 158 against the resistance of spring 152 and up through inner medial bore 148 through throttling orifice 150 in inner medial bore 148 and out through sampler shutoff valve 46 into sample flow line 48.

It is apparent that the sampler can be constructed of a variety of materials, depending on its intended use. For example, for use in an oil pipeline the sampler could be made of materials to withstand substantial fluid pressure and which are corrosion resistant. Similarly, it is apparent that the sampler could be mounted on or near the pipeline in a variety of ways.

It is further apparent that a variety of means can be used to actuate piston movement, including but not limited to manual, mechanical, hydraulic, pneumatic, or electromechanical means.

It is still further apparent that the sampler can be enclosed in a housing, and can be connected to the pipeline in a variety of fashions so long as the interior of the pipeline communicates with the interior of the common passageway sufficiently to allow sampling and to allow flow through the sample chamber when not actively sampling. In like fashion, it is apparent that the pistons could be of a variety of shapes consistent with motion in the common passageway and with periodically sealing off the lateral input and outlet ports.

It is further apparent that the nature of the pipeline and the fluid contained in the pipeline are irrelevant to the broad aspects of the invention and that the sampler of the invention may be used to sample a wide variety of fluids in a wide variety of conduits or containers. For example, the sampler could be used in biomedical fluid lines to sample body fluids or to sample medications to monitor and confirm optimum health treatment conditions. Likewise, the sampler could be used in water lines or in water additive lines to monitor and confirm optimum water treatment conditions. The sampler could be used in chemical transport lines of all types to monitor and confirm the composition of the chemicals being transported. The sampler could take single samples and then discontinue until reset or could intermittently take samples until a sample chamber is full. The operation of the pistons to seal off a sample chamber and then drive the sample out through a sample port makes the unit substantially independent of pressure, as the sampler will capture the fluid at whatever pressure it is at in the chamber at the time the inlets and outlets are sealed to create the sample chamber. The pistons will then elevate the pressure of the captured sample sufficiently to force it out through the sampler port and into the sample container. The force of the pistons makes the sampler also independent of sample container, as the pistons have sufficient power to overcome any sample pressure up to a pressure relief or burst disc setting constituting the maximum sample chamber pressure.

Accordingly, it is also apparent from the foregoing that the present invention is not limited to the embodiments shown. Other equally effective embodiments are contemplated and within the scope of the present invention.

What is claimed is:

1. A sampler for transferring samples between an exterior region and a pipeline, comprising:
   a plurality of pistons,
   a body having a common passageway in which said pistons are slidably mounted,
   a lateral inlet and a lateral outlet port located within said passageway and communicating with the pipeline, said inlet and outlet ports situated so that motion of said pistons can cover and uncover said inlet and outlet ports, and
   a lateral sample port situated between said inlet and outlet ports and communicating with said common passageway.

2. The sampler of claim 1, wherein the pistons are opposed.

3. The sampler of claim 1, wherein the pistons are disposed on opposite sides of the sample port and are adapted to move across and close the inlet and outlet ports during movement toward the sample port, to thereby define a sample chamber between the opposed pistons.

4. The sampler of claim 3, wherein the common passageway comprises a sample chamber sleeve.

5. A sampler for transferring samples between an exterior region and a pipeline, comprising:
   a plurality of pistons,
   a body having a common passageway in which said pistons are slidably mounted,
   a lateral inlet and a lateral outlet port located within said passageway and communicating with the pipeline, said inlet and outlet ports situated so that motion of said pistons can cover and uncover said inlet and outlet ports, and
   a lateral sample port situated between said inlet and outlet ports and communicating with said common passageway, wherein the lateral inlet port is at an oblique angle with respect to the common passageway.

6. The sampler of claim 5, wherein the lateral outlet port is at an oblique angle with respect to the common passageway.

7. The sampler of claim 1, wherein the lateral outlet port is at an oblique angle with respect to the common passageway.

8. The sampler of claim 2, further comprising:
   a spacer to stop the movement of only one of the two opposed pistons a predetermined distance from, but adjacent to, the sample port;
   a fluid power supply line to each of the pistons from a single pressure source; and
   a restriction in the fluid power supply line to a first one of the pistons sufficient to make that first one of the pistons move slower than the other of the two pistons, so as to cause a sample chamber to be formed between the two pistons as they move toward each other at different speeds, and then stopping the second piston due to contact with the spacer, while still allowing the slower first one of the two pistons to continue moving toward the other stopped in a second piston, so as to subsequently force the contents of the sample chamber into the lateral sample port.

9. A sampler for transferring samples between an exterior region and a pipeline, comprising:
   a plurality of pistons;
   a body having a common passageway in which said pistons are slidably mounted;
   a lateral inlet and a lateral outlet port located within said passageway and communicating with the pipeline, said inlet and outlet ports situated so that motion of said pistons can cover and uncover said inlet and outlet ports;
   a lateral sample port situated between said inlet and outlet ports and communicating with said common passageway, and
   delay means for causing the pistons to move at different rates under the action of fluid pressure.

10. The sampler of claim 9, wherein the delay means is a difference in spring constants between springs contacting the pistons.

11. The sampler of claim 9, wherein the delay means comprises a reduced diameter in a fluid power supply to one of the pistons relative to the diameter of a fluid power supply to the other of the pistons.

12. The sampler of claim 11, wherein the delay means comprises an orifice in the fluid power supply to only one of the two pistons.

13. A sampler for transferring samples between an exterior region and a pipeline, comprising:
   a plurality of pistons;
   a body having a common passageway in which said pistons are slidably mounted;
   a lateral inlet and a lateral outlet port located within said passageway and communicating with the pipeline, said inlet and outlet ports situated so that motion of said pistons can cover and uncover said inlet and outlet ports; and a lateral sample port situated between said inlet and outlet ports and communicating with said common passageway;

wherein the pistons are differential pistons which have a smaller diameter portion in fluid communication with the common passageway and a larger diameter portion not in fluid communication with the common passageway, and a vented portion between the larger and smaller.

14. The sampler of claim 13, further comprising a spring disposed inwardly of a portion of at least one of the pistons and adapted to yieldably resist movement of that one piston into the common passageway, and wherein the larger diameter portion of that one piston is adapted to be selectively placed in fluid communication with pipeline pressure to so as move that one piston toward the common passageway against the resistance of the spring due to a force differential resulting from the difference in diameters.

15. The sampler of claim 14 wherein the pressure in the common passageway is the same as in the pipeline, whereby the pistons are forced toward the common passageway by virtue of the difference in diameter between the portions without need for external power supply to move the pistons.

16. The sampler of claim 14, wherein the inlet flow line has a bend at the upstream end for allowing the inlet flow line to be directed radially into the pipeline transverse to the direction of flow and the upstream end facing upstream into the flow path.

17. The sampler of claim 1, wherein the sampler comprises:

an inlet flow line communicating with the pipeline and the lateral inlet port, and an outlet flow line communicating with the lateral outlet port and the pipeline.

18. A sampler for transferring samples between an exterior region and a pipeline, comprising:

a plurality of pistons;

a body having a common passageway in which said pistons are slidably mounted;

a lateral inlet and a lateral outlet port located within said passageway and communicating with the pipeline, said inlet and outlet ports situated so that motion of said pistons can cover and uncover said inlet and outlet ports;

a lateral sample port situated between said inlet and outlet ports and communicating with said common passageway;

an inlet flow line communicating with the pipeline and the lateral inlet port, and an outlet flow line communicating with the lateral outlet port and the pipeline; a primary first piston supply line in fluid communication with the outlet flow line and with a surface of a first one of the pistons; and a second piston supply line in fluid communication with the outlet flow line and with a surface of a second one of the pistons.

19. The sampler of claim 18, further comprising a secondary first piston supply line in fluid communication with the outlet flow line and with said surface of said first one of the pistons to thereby help prevent the second piston from moving faster than the first piston.

20. The sampler of claim 18, wherein the pistons are differential pistons powered by fluid pressure in the outlet flow line.

21. The sampler of claim 18 wherein the primary first piston supply line serves as the communication between the outlet line and the second piston supply line.

22. The sampler of claim 21, further comprising an orifice in the portion of the primary first piston supply line between the second piston supply line and the first piston, whereby the pistons are caused to move at different rates by an orifice on the outlet flow line.

23. The sampler of claim 21, further comprising a timer which generates a timed signal and a valve in the portion of the primary first piston line between the second piston supply line and the outlet flow line, said valve being normally closed but adapted to open in response to said timed signal.

24. The sampler of claim 21, further comprising a pressure regulator valve in the primary first piston supply line and adapted to regulate the pressure in the first piston supply line and second piston supply line.

25. The sampler of claim 24, wherein the pressure regulator valve is responsive to pressure in the primary first piston supply line.

26. The sampler of claim 24, further comprising:

a sample cylinder line in fluid communication with the lateral sample port;

a check valve in the sample port adapted to prevent fluid flow from said sample cylinder line into the sample outlet port while allowing fluid flow from said sample outlet port into said sample cylinder line; and a sensor line in communication with the sample cylinder line and the pressure regulator valve, the regulator valve being adapted to prevent fluid flow through said piston supply lines responsive to a given pressure being reached in the sensor line.

27. A sampler for transferring samples between an exterior region and a pipeline, comprising:

a plurality of pistons;

a body having a common passageway in which said pistons are slidably mounted;

a lateral inlet and a lateral outlet port located within said passageway and communicating with the pipeline, said inlet and outlet ports situated so that motion of said pistons can cover and uncover said inlet and outlet ports;

a lateral sample port situated between said inlet and outlet ports and communicating with said common passageway; and a spring between the body and at least one of the pistons, the spring being adapted to bias the piston in a direction away from the common passageway.

28. The sampler of claim 27, further comprising an inner end cap surrounding and retaining an inner end of said spring adjacent to but outside of the common passageway.

29. The sampler of claim 4 wherein the common passageway further comprises a second sample chamber sleeve, each of said sleeves surrounding an inner portion of one of said pistons.

30. The sampler of claim 16, wherein the inlet flow line is disposed in the pipeline upstream of the outlet line port.

31. The sampler of claim 30, wherein the flow line inlet further comprises a pitot tube.

* * * * *